United States Patent
Hornung et al.

(10) Patent No.: US 7,988,357 B2
(45) Date of Patent: Aug. 2, 2011

(54) X-RAY SYSTEM

(75) Inventors: Oliver Hornung, Fürth (DE); Jochen Miguel Löseken, Erlangen (DE); Michael Meyer, Hausen (DE)

(73) Assignee: Siemens Aktiengesellschaft, Munich (DE)

( * ) Notice: Subject to any disclaimer, the term of this patent is extended or adjusted under 35 U.S.C. 154(b) by 83 days.

(21) Appl. No.: 12/497,244

(22) Filed: Jul. 2, 2009

(65) Prior Publication Data
US 2010/0008474 A1  Jan. 14, 2010

(30) Foreign Application Priority Data
Jul. 9, 2008  (DE) .................. 10 2008 032 294

(51) Int. Cl.
H05G 1/02 (2006.01)
H05G 1/00 (2006.01)
(52) U.S. Cl. .......................... 378/197; 378/204
(58) Field of Classification Search .............. 378/4–20, 378/189, 193, 194, 197, 198, 204, 205
See application file for complete search history.

(56) References Cited

U.S. PATENT DOCUMENTS

| | | | | |
|---|---|---|---|---|
| 4,501,011 A * | 2/1985 | Hauck et al. | | 378/196 |
| 6,200,024 B1 * | 3/2001 | Negrelli | | 378/197 |
| 6,582,121 B2 * | 6/2003 | Crain et al. | | 378/197 |
| 7,354,196 B2 * | 4/2008 | Boese et al. | | 378/190 |
| 2003/0112926 A1 * | 6/2003 | Atzinger | | 378/196 |
| 2010/0266104 A1 * | 10/2010 | Van Der Ende | | 378/197 |

FOREIGN PATENT DOCUMENTS

| | | |
|---|---|---|
| DE | 102 15 987 A1 | 11/2003 |
| DE | 10 2006 029 198 A1 | 11/2007 |
| DE | 10 2006 028 326 A1 | 1/2008 |
| DE | 10 2006 041 033 A1 | 3/2008 |
| EP | 0 220 501 B1 | 5/1989 |
| WO | WO 2007/026282 A2 | 3/2007 |

OTHER PUBLICATIONS

German Office Action dated Feb. 25, 2009 with English translation. Presseinformation der Siemens AG vom Feb. 28, 2005: "Europapremiere beim ECR: Angiographische C-Bogen-Systeme von Siemens generieren CT-ähnliche Schnittbilder" (http://www.forum-deutsche-medizintechnik.de/mediletter/archiv/2005_2/siemens_2.php) = alt http//w1.siemens.com/ press/de/pp_med/2005/medax200503008_04(dynact)_124738 . . . = neu; Others; 2005; DE.

* cited by examiner

*Primary Examiner* — Anastasia Midkiff
(74) *Attorney, Agent, or Firm* — Lempia Summerfield Katz LLC

(57) ABSTRACT

An x-ray system is provided. The x-ray system includes an x-ray emitter which can be adjusted by at least one arm as a first x-ray component and a recording system which can be adjusted independently of the at least one arm. The recording system may be adjusted by at least one additional arm as the further x-ray component. The two arms can be pivotably mounted about a common axis of rotation.

12 Claims, 1 Drawing Sheet

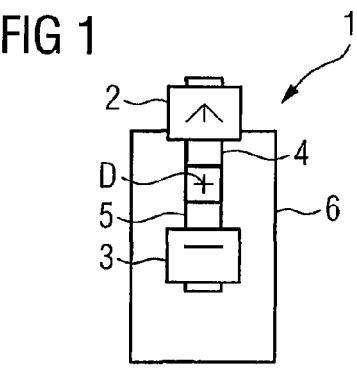
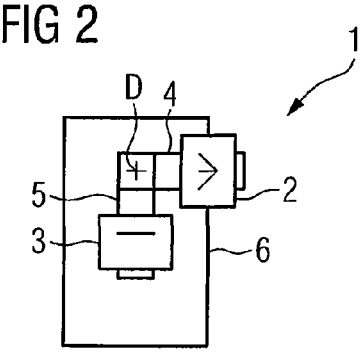
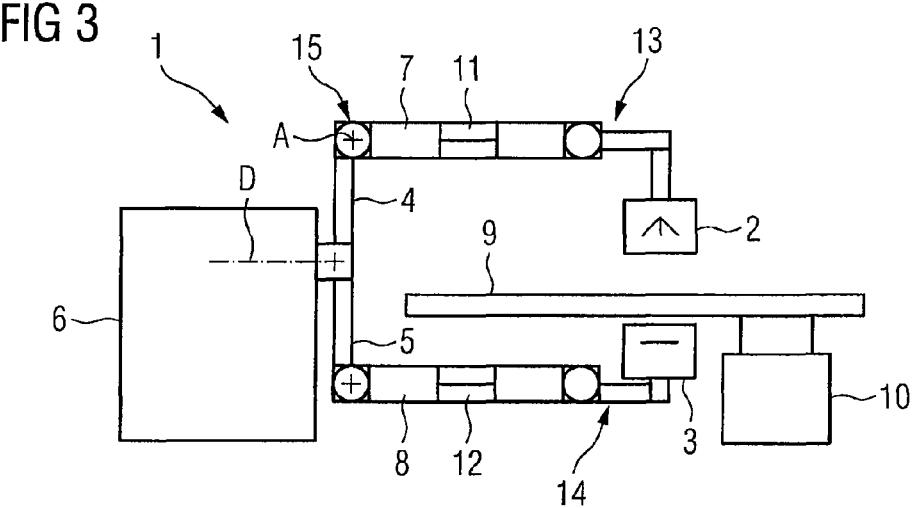
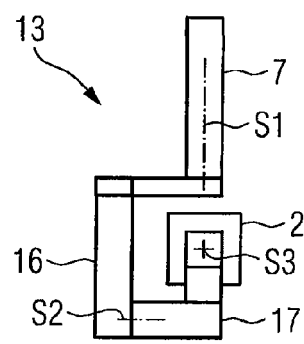
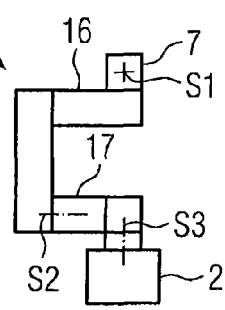

X-RAY SYSTEM

This patent document claims the benefit of DE 10 2008 032 294.6 filed Jul. 9, 2008, which is hereby incorporated by reference.

BACKGROUND

The present embodiments relate to an x-ray system (facility).

EP 0 220 501 B1 discloses an x-ray system that has adjustment device for adjusting different system components. The adjustment device may be robot arms. In addition to an x-ray tube and an image recording system, a patient support is also be adjusted with the robot arm. The x-ray system known from EP 0 220 501 B1 requires a lot of space.

C-arm x-ray devices represent a widespread type of x-ray devices. The C-arm may support an x-ray source and an assigned detector. DE 102 15 987 A1 discloses that the C-arm may be coupled in a moveable fashion to a moveable unit. DE 10 2006 028 326 A1 and in DE 10 2006 041 033 A1 discloses using an articulated arm robot to control a C-arm of an x-ray system. The robot arm allows the x-ray source and the x-ray detector to be moved on a defined path around the patient.

C-arm x-ray devices are typically designed for the flexible, but static production of projection recordings. Computed tomography devices operating with x-ray radiation sources circulating about an axis or rotation along a circumferential ring are used to generate cross-sectional image recordings, as disclosed in DE 10 2006 029 198 A1. In subareas, computed tomography devices can be replaced by C-arm x-ray devices including an extended functional scope, which can generate cross-sectional images with 10 mm thick layers. Reference is made to the press release by Siemens AG dated Feb. 28, 2005 entitled "Europapremiere beim ECR: Angiographische C-Bogen-Systeme von Siemens generieren CT-ähnliche Schnittbilder" [European premiere with ECR: angiographic C-arm systems by Siemens generate CT-like cross-sectional images] (http://www.forum-deutsche-medizintechnik.de/mediletter/archiv/2005_2/siemens_2.php). The C-arm systems operating using flat-panel detector technology and introduced in the press release are provided for use during an intervention, for example, a neuroradiological, abdominal, or oncological intervention. The C-arm systems display high-contrast image contents and allow for soft tissue differentiations. Cross-sectional images are generated from image sequences, which were obtained with a recording system that can be displaced along a trajectory. The reconstruction quality does not achieve the quality that can be obtained using a computed tomography device. In addition, no complete rotation of the image recording system is possible.

SUMMARY AND DESCRIPTION

The present embodiments may obviate one or more of the limitations or drawbacks inherent in the related art. For example, in one embodiment, an x-ray system has a compact design, rational producibility, and versatile applicability.

As used herein, "kinematics" may include movements.

In one embodiment, an x-ray system may be used as a medical-specific diagnostic device. The x-ray system includes an x-ray emitter and an associated recording system, such as a flat-panel detector. The x-ray emitter and the recording system, which may be referred to collectively or individually as x-ray components, are supported directly or indirectly by at least one arm. The at least one arm may support the x-ray components being pivotable about a common axis. If a straight angle is drawn between the arms, the arms and x-ray components may form a C-arm arrangement, which, with respect to the geometry, in static terms, may be compared with conventional C-arm x-ray devices. One difference between conventional x-ray devices is the two arms forming parts of a C-arm divided on the axis of rotation, so that higher flexibility is easily provided. The x-ray system is suited, for example, to standard angiography applications and to extended angiography applications. The x-ray system provides for user and patient-friendly interoperative imaging.

The separate adjustability of the x-ray source and the associated recording system is advantageous in that no adjusting mechanism is required in contrast to a C-arm x-ray device, the adjusting device being designed to move a heavy machine part, such as a C-arm, supporting both the x-ray source and also the x-ray detector as a whole. Instead, a special drive is present for the adjustment of the x-ray emitter supported by a pivotable arm and the adjustment of the recording system supported by an additional pivotable arm. The drive may have a relatively minimal weight. The x-ray system, which, instead of a rigid C-arm, has two sub kinematic devices, is structured in a weight-saving fashion compared with a conventional C-arm x-ray device.

If an arm of the x-ray system supporting only one individual x-ray component, for example, either the x-ray source or the recording system, is considered as the robot arm, a final effector coordinate system of the relevant robot arm is provided by the x-ray source and/or the recording system in each instance. During conventional operation of the x-ray system, a constant relative transformation is provided between the two end effector coordinate systems. Accordingly, the recording system may be in a stationary position relative to the x-ray source. Common ground exists between the x-ray system and a C-arm x-ray device. The C-arm may be fastened to the end effector, provided an adjustment is provided by a robot arm. Even with a rigid configuration of such a robot-controlled C-arm system, dynamic effects when adjusting the C-arm play a significant role. Such effects must, if actually possible, be detected and corrected in complicated simulation and/or test procedures. Even without negatively affecting dynamic effects during the adjustment of a C-arm, the deviation of the position of robot components from the theoretical position, which occurs as a result of the mass to be moved, results in a significant reduction in the quality of the data generated. Disadvantages of this type are largely limited in the case of the special sub kinematics for the x-ray source as well as for the x-ray system comprising the recording system. With a simpler structure compared with a robot-controlled C-arm x-ray system, significantly faster adjustment movements, for example, swiveling or rotational movements with more than about 120°/s, can be realized using the x-ray system.

The arms which can be pivoted about the common axis of rotation may be moveable in a plane which is normal with respect to the axis of rotation. Other embodiments may be realized, in which the arms operable to be pivoted about the common axis of rotation, also referred to as inner arms, do not draw a right angle or draw a variable angle with the axis of rotation. Provision is advantageously made to rotate the arms supporting the x-ray components by more than 360°, for example, in an unlimited fashion, about the common axis of rotation. In the event of unlimited rotatability, provision may be made for energy and/or signals to be transmitted to the x-ray components, for example, with contact rings.

In one embodiment, an additional outer arm supporting the assigned x-ray components, at least indirectly, is connected to each of the inner arms which may be pivoted about the common axis of rotation by a hinge. The hinge may have an axis which is aligned orthogonally with respect to the common axis of rotation, with the axes of the two hinges being arranged between the inner and the outer arms in parallel to one another, provided the two inner arms are arranged along a single line.

Each additional outer arm may be adjustable in length, for example, with an electromechanical or hydraulic adjustment element. Depending on the operating mode of the x-ray system, the length of the outer arm is constantly maintained or automatically varied during the swiveling (<360°) or rotation (>360°) of the x-ray components.

The x-ray components (e.g., the x-ray source and the associated x-ray detector) may be connected to the outer arm by a hinge arrangement. The hinge arrangement may include several, in particular three, swiveling axes. Each of the swiveling axes may be arranged at right angles on at least one additional swiveling axis of the relevant hinge arrangement. On the whole, six (6) point adjustability of each x-ray component is provided in this embodiment. The corresponding axes are adjustment axes, with the specified sequence reproducing the kinematic chain: the common axis of rotation, the axis between the inner and outer arm, the linear adjustment element of the outer arm, and the three axes of the hinge arrangement between the outer arm and the x-ray components supported hereby. Since the position of the second x-ray component during conventional operation is determined by the position of the first x-ray component, the overall kinematic system has effectively six degrees of freedom.

The x-ray system provides a conceptual separation of a rigid C-arm of an x-ray device into two sub kinematics having a common axis of rotation. The x-ray system offering applications in the case of a relatively simple design by comparison with conventional C-arm x-ray devices, which are not given by a C-arm x-ray device, nor by a computed tomography device which is structured in a complex fashion. By comparison with a computed tomography device, the improved accessibility of the examination region is particularly important.

BRIEF DESCRIPTION OF THE DRAWINGS

FIG. 1 shows one embodiment of a medical-specific x-ray system in a first front view, FIG. 2 shows one embodiment of the x-ray system according to FIG. 1 in a second front view, FIG. 3 shows the x-ray system and a patient support in the side view, FIG. 4 shows one embodiment of a hinge of the x-ray system in a first view, and FIG. 5 shows the hinge according to FIG. 4 in a second view.

DETAILED DESCRIPTION

In one embodiment, an x-ray system 1 includes an x-ray emitter 2 and an associated recording system 3, such as a semi-conductor flat-panel detector. The x-ray emitter 2 and the recording system 3, which may be referred to as x-ray components, are indirectly held (supported) by a moveable arm 4, 5. The two arms 4, 5 are rotatable about a common axis of rotation D, which is fixed in a stationary fashion relative to a machine part 6 which can be anchored to or moved on the base for instance.

In the arrangement according to FIG. 1, a 180° angle is drawn between the arms 4, 5 of the x-ray system 1. The arms 4, 5 are aligned orthogonally to the axis of rotation D. The x-ray system 1 may be used like a conventional C-arm x-ray device, for example, for angiography. In contrast to a conventional C-arm x-ray device, any rotation (about an angle of more than 360°) of the C-shaped arrangement, which includes arms 4, 5 and x-ray components 2, 3, about the axis of rotation D is possible.

FIG. 2 illustrates the adjustment options provided. During the actual operation of the x-ray system 1, the recording system 3 is aligned relative to the x-ray emitter 2, such that the functions of the recording system 3, such as the detection of the x-rays, may be fulfilled. The distance between the x-ray emitter 2 and the recording system 3 may remain constant.

FIG. 3 shows an overview of the different possibilities of adjusting the x-ray components 2, 3 relative to one another and relative to the typically stationary machine part 6. An outer arm 7, 8 is moveably coupled to each of the inner arms 4, 5 that can rotate about the axis of rotation D, with the axis A formed between an inner arm 4, 5 and an outer arm 7, 8 and with each position of the inner arm 4, 5 running orthogonally to the common axis of rotation D, for example, in a tangential direction of a circle, the center point of which rests on the common axis of rotation D.

The outer arms 7, 8 are arranged above and/or below a patient support (bed) 9 in the arrangement according to FIG. 3. The patient support may be adjustably mounted on a frame 10. The inner arms 4, 5 can be hinged on the frame 10 of the patient support 9 so that the machine part 6 is identical to the frame 10.

Each outer arm 7, 8 has an adjusting apparatus 11, 12, which enables a telescope-type adjustment in length of the respective arm 7, 8. The x-ray emitter 2 and/or the recording system 3 is fastened to the outer arm 7, 8 by a hinge arrangement 13, 14. Contrary to the hinge 15 formed in each instance between an inner arm 4, 5 and an outer arm 7, 8, the hinge arrangements 13, 14 allow multiaxial swiveling movements. The hinge arrangements 13, 14 are shown symbolically in FIG. 3.

The function of the hinge arrangements 13, 14 are illustrated in FIGS. 4, 5. FIGS. 4 and 5 relate to the hinge arrangement 13 connecting the x-ray emitter 2 to the outer arm 7. The main structure of the hinge arrangement 14, which connects the recording system 3 to the outer arm 8, is also shown.

FIG. 4 shows the hinge arrangement 13 in the line of sight at right angles from above onto the patient support 9 (FIG. 3). An inner connecting piece 16, which is bent several times, is pivotably connected to the end of the outer arm 7 facing away from the inner arm 4, with the corresponding pivoting axis S1 being aligned in the arrangement according to FIGS. 3 and 4 along the outer arm 7 and in parallel to the common axis of rotation D. A further outer connecting piece 17 is pivotably connected to the inner connecting piece 16. A pivoting axis S2 may run orthogonally to the first pivoting axis S1. The outer connecting piece 17 is connected in a hinge-like fashion to the x-ray emitter 2, with a swiveling axis S3, about which the x-ray emitter 2 can be pivoted relative to the outer connecting piece 17. The connecting piece 17 may be arranged orthogonally to the second swiveling axis S2. In the arrangement according to FIGS. 4 and 5, the swiveling axis' S1, S2, S3 are arranged at right angles to one another. FIG. 5 shows the arrangement according to FIG. 4 with a viewing direction in parallel with the common axis of rotation D. The x-ray emitter 2 may be arranged vertically above the patient support 9.

As shown in FIGS. 3 to 5, the x-ray system 1 differs significantly from the design of current articulated arm robots with respect to the spatial arrangement of the elements which can be adjusted relative to one another. Segments of the robot arm, which are arranged in a V-shaped fashion with respect to one another, are typical for robots, with it being possible to draw angles, which are significantly less than 90° and also angles, which are significantly greater than 90° between the segments. In the case of articulated arm robots, kinematic singularities may result, which signify the omission of a degree of freedom and are to be avoided in practice. The x-ray system 1, however, during conventional operation, prevents kinematic singularities due to the geometric structure. Special safety precautions taken to avoid kinematic singularities are not necessary. The implementation of safety systems, such as collision avoidance systems, which contribute to avoiding injury to persons due to moving machine parts, such as the outer arms 7, 8 with the x-ray components 2, 3 held hereupon, may be included.

During an adjustment of the x-ray emitter 2, the recording system 3 may be automatically adjusted so that the recording system 3 is aligned in parallel with the x-ray emitter 2. The relationship between the adjustment of the different x-ray components 3, 4 is not produced by mechanical connecting elements or drives, but instead in a control-specific, such as software-specific, manner. The adjustment kinematics provided for this reason in the case of the x-ray system 1 is also referred to as pseudo parallel kinematic.

The pseudo parallel kinematics allows the x-ray components 2, 3 to be moved on different paths. For example, if the inner arms 4, 5 are left in the position shown in FIGS. 1 to 3 relative to one another (i.e., opposite to one another diametrally) and the remaining elements 11-15 enabling linear or rotational adjustments are not adjusted during an examination implemented with the x-ray system 1, the x-ray components 2, 3 can be moved on a circular path positioned about the patient support 9.

An exclusive adjustment of the linear adjusting apparatuses 11, 12 allows different projections to be recorded, which can also be acquired in a similar fashion by the patient support 9 being moved in its longitudinal direction.

Restricted adjustment options of the x-ray system 1 may be sufficient. For example, applications exist, in which, compared with the exemplary embodiment illustrated in FIGS. 1 to 5, restricted adjustment options of the x-ray system 1 are sufficient.

A move complex operating mode, which enables the x-ray system 1, may be used for displacing the x-ray components 2, 3 on linear paths, which run essentially at right angles to the common axis of rotation D and to the patient support 9. The angle drawn between the inner arms 4, 5 permanently changes during the displacement of the x-ray components 2, 3. The remaining adjustable elements 11-15 may be automatically actuated at the same time in a fashion attuned to one another in order to adjust the x-ray components 2, 3 in the desired manner.

Simultaneous actuation of several differently adjustable elements 11-15 is also provided when the x-ray components 2, 3 are moved on the spiral-shaped trajectories. Three-dimensional data records may be generated. The three-dimensional data may be rudimentally obtained using C-arm devices, generally however only with computed tomography devices. Depending on the type of x-ray examination carried out using the x-ray system 1, the isocenter of the examination may optionally be held in a constant position or assume variable positions.

The versatile adjustment options of the x-ray emitter 2 and of the recording system 3 of the x-ray system 1, which are largely independent from one another, may allow the generation of cross-sectional images, the plane of which does not draw a right angle with the axis of rotation D. The x-ray emitter 2 may be moved on a non-circular, for example, elliptical path, around the examination object. With this movement, the distance between the x-ray emitter 2 and the recording system 3, may be kept automatically constant. Provided the ellipse described by the trajectory of the x-ray emitter 2 is arranged symmetrically to the axis of rotation D, in this operating mode, the recording system 3 is at less of a distance from the axis of rotation D, the further the x-ray emitter 2 is distanced therefrom.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. An x-ray system comprising:
   an x-ray emitter that is operable to be adjusted by a first arm;
   a recording system that is operable to be adjusted independently of the first arm, the recording system being adjusted by a second arm; and
   an additional arm that indirectly supports at least one of the x-ray emitter and the recording system, the additional arm being connected to the first arm or the second arm and operable to be pivoted about a common axis of rotation using a hinge, wherein the at least one of the x-ray emitter and the recording system is connected to the additional arm by a hinge arrangement,
   wherein the first arm and the second arm are pivotably mounted to the common axis of rotation, and
   wherein the hinge arrangement comprises three swiveling axes.

2. The x-ray system as claimed in claim 1, wherein the first arm and the second arm form a C-arm with the first arm and the second arm being positioned opposite one another.

3. The x-ray system as claimed in claim 2, wherein the first arm and the second arm extend orthogonally to the common axis of rotation.

4. The x-ray system as claimed in claim 1, wherein the hinge is operable to be moved about a hinge axis, which runs orthogonally to the common axis of rotation.

5. The x-ray system as claimed in claim 1, wherein the additional arm is adjustable in length.

6. The x-ray system as claimed in claim 1, wherein the swiveling axes are arranged orthogonally to one another.

7. The x-ray system as claimed in claim 1, wherein the recording system includes a flat panel detector.

8. An x-ray system comprising:
   an x-ray emitter that is operable to be adjusted by a first arm;
   a recording system that is operable to be adjusted independently of the first arm, the recording system being adjusted by a second arm, wherein the first arm and the second arm are pivotably mounted about a common axis of rotation; and
   an additional arm that indirectly supports at least one of the x-ray emitter and the recording system, the additional arm being connected to the first arm or the second arm and operable to be pivoted about the common axis of rotation using a hinge, wherein the at least one of the x-ray emitter and the recording system is connected to the additional arm by a hinge arrangement,
   wherein the hinge arrangement comprises three swiveling axes, wherein the first arm and the second arm form at least part of a C-arm with the first arm being positioned opposite to the second arm, and wherein the first arm and the second arm extend orthogonally to the common axis of rotation.

9. The x-ray system as claimed in claim 8, wherein the hinge is operable to be moved about a hinge axis, which runs orthogonally to the common axis of rotation.

10. The x-ray system as claimed in claim 8, wherein the additional arm is adjustable in length.

11. The x-ray system as claimed in claim 8, wherein the swiveling axes are arranged orthogonally to one another.

12. The x-ray system as claimed in claim 8, wherein the recording system includes a flat panel detector.

* * * * *